United States Patent [19]

Cummins et al.

[11] Patent Number: 4,516,353

[45] Date of Patent: * May 14, 1985

[54] METHOD OF PRODUCING VOLE-RESISTANT APPLE TREES AND TREES PRODUCED THEREBY

[75] Inventors: James N. Cummins; Herb S. Aldwinckle, both of Geneva, N.Y.; Ross E. Byers, Winchester, Va.

[73] Assignee: Cornell Research Foundation, Inc., Ithaca, N.Y.

[*] Notice: The portion of the term of this patent subsequent to Nov. 13, 2001 has been disclaimed.

[21] Appl. No.: 391,770

[22] Filed: Jun. 24, 1982

[51] Int. Cl.$^3$ ............................................. A01H 1/00
[52] U.S. Cl. ............................................. 47/58; 47/6
[58] Field of Search ........................................ 47/6-7, 47/58; Plt./34-35

[56] References Cited

PUBLICATIONS

Proceedings of the Fourth Eastern Pine and Meadow Vole Symposium, Feb. 21-22 1980, pp. 43-49 and 50-54.
Wysolmerski et al., J. Am. Soc. Hort. Sci., 105:675-677, 1980.
1977 Transactions Ill. State Hort. Soc., 110:45-56, (1977).
Cummins et al., New York's Food & Life Sciences Bull. No. 41, May 1974, pp. 1-15.
Byers et al., J. Am. Soc. Hort. Sci., 102(2):201-203, (1977).

Primary Examiner—Robert E. Bagwill

[57] ABSTRACT

The present invention relates to novel propagated apple trees having increased vole resistance and to methods for propagating such trees; and relates in one aspect to an apple tree having a vole-resistant rootstock and having growing thereon a desired apple bearing scion. In a preferred embodiment, the vole-resistant rootstock has a characteristic modifying distinct interstem interposed between the apple bearing scion and the rootstock. In another embodiment of the invention, the stocksystem is a composite stocksystem wherein a portion of the stocksystem is of a variety (seedling or other rootstock) distinct from the vole-resistant stock and wherein the portion of the rootstock above ground and to which the scion or interstem is grafted, comprises the novel vole-resistant stock. The nature of the companion rootstock is not critical and any compatible rootstock such as those already known in the art, for example, from "Delicious seedlings" can be employed. The systems proposed in the present invention present apple trunk tissue to voles which is unpalatable to them.

7 Claims, 4 Drawing Figures

METHOD OF PRODUCING VOLE-RESISTANT APPLE TREES AND TREES PRODUCED THEREBY

BACKGROUND OF THE INVENTION

The pine vole is a major hazard to apple trees in the Cumberland—Shenandoah region of the eastern United States, western North Carolina and eastern New York. A recent study in Henderson County, North Carolina, revealed that this animal was the most serious cause of apple tree mortality. Although less damaging because more easily controlled by chemical and cultural means, the meadow vole is also an important hazard to apple growing throughout the eastern United States; see Proceedings of the Fourth Eastern Pine and Meadow Vole Symposium-Feb. 21–22, 1980, where the use of vole-resistant stock systems are discussed.

Wysolmerski et al, J. Amer. Soc. Hort. Sci., 105:675–677 (1980), describe laboratory evolution of Malus cultivars and hybrids for susceptibility to damage from pine voles.

Cummins et al, "Multiple-Stock Apple Trees", Transactions of the Illinois State Horticultural Society and the Illinois Fruit Council - 1976, describe multi-stock apple trees, e.g. trees with distinct rootstocks and interstems, under a fruiting top.

Cummins et al, "Apple Rootstock Problems and Potentials", New York's Food and Life Sciences Bulletin No. 41, May 1974, discuss the use of clonal rootstocks.

Co-pending plant patent application Ser. No. 391,897 filed June 6, 1982 by James N. Cummins, Herb S. Aldwinckle and Ross E. Byers, entitled "Apple Tree" describes a new and distinct apple clone (a seedling of *Malus prunifolia*) discovered in a test planting belonging to New York State Agricultural Experiment Station, Cornell University, Geneva, Ontario County, New York. This apple clone is the preferred rootstock employed in the trees of this invention. The above-identified application is hereby incorporated by reference.

BRIEF DESCRIPTION OF THE DRAWINGS

The four FIGURES schematically present various composite trees which exemplify embodiments of the invention.

DESCRIPTION OF THE INVENTION

Figure 1:
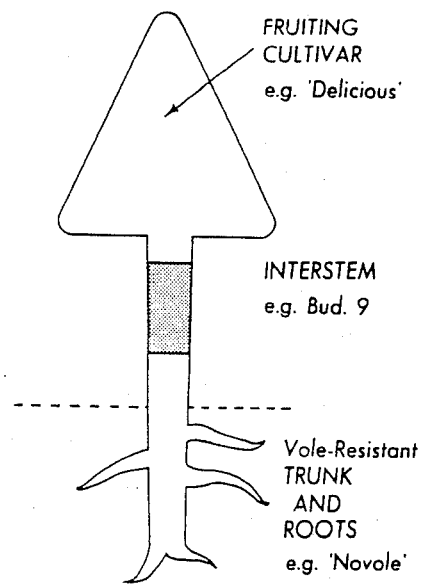

The present invention relates to novel propagated apple trees having increased vole resistance and to methods for propagating such trees; and relates in one aspect to an apple tree having a vole-resistant rootstock and having growing thereon a desired apple bearing scion. In a preferred embodiment, the vole-resistant rootstock has a characteristic modifying distinct interstem interposed between the apple bearing scion and the rootstock. In another embodiment of the invention, the stocksystem is a composite stocksystem wherein a portion of the stocksystem is of a variety (seedling or other rootstock) distinct from the vole-resistant stock and wherein the portion of the rootstock above ground and to which the scion or interstem is grafted, comprises the novel vole-resistant stock. The nature of the companion rootstock is not critical and any compatible rootstock such as those already known in the art, for example, from "Delicious seedlings" can be employed. The essence of all the systems proposed in the present invention is to present to voles only apple trunk tissue which is unpalatable to them.

Since the vole-resistant clone employed in this invention is very vigorous when employed as stock, and since the modern apple grower usually requires half-standard trees, generally either a dwarfing interstem clone with a fruiting cultivar or a genetically dwarf scion cultiver is employed.

The vole-resistant rootstock or bridging stock employed in the composite trees of this invention can be any Malus clone proved by laboratory and/or field testing to be resistant, either by non-preference or by other mode, to pine vole and/or to meadow vole. Specifically included are the asexual propagules of the tree described in the above-identified plant patent (hereinafter referred to as 'Novole'), *Malus robusta* cv. No. 5 ('Robusta 5'), *M.X micromalus*, and *M.X spectabilis*. The vole-resistant stock is propagated asexually on its own roots by cuttage, by stooling, by nurse root grafting or by micropropagation. Normally such a vole-resistant clone will be displayed as both root and trunk stock. However, a composite stocksystem composed of a non-resistant rootstock grafted with the vole-resistant stock can be employed wherein the trunk emerging from the ground, on which the remainder of the tree is formed, comprises the vole-resistant clone. The height of the rootstock where grafted is not unduly critical, beyond the fact that it is desired to present an adequate vole-resistant segment to retard vole damage. When forming the tree, usually the vole-resistant rootstock extends to between about 12 and 18 inches above soil level at which point either the interstem or the scion cultivar is grafted.

The preferred vole-resistant rootstock or bridging stock employed in producing the apple trees of this invention is Novole, a new and distinct vegetatively propagated cultivar of apple tree ( a selection of PI 286613) which we discovered in a test planting belonging to New York State Agricultural Experiment Station, Cornell University, Geneva, Ontario County, New York. Rigorous testing of this clone in our laboratories, greenhouses, nurseries and orchards revealed that it is resistant to *Erwinia amylovora* (fire blight), *Phytophthora cactorum* (crown rot), *Venturia inaequalis* (apple scab), *Microtus pinetorum* (pine vole) and *M. pennsylvanicus* (meadow vole), all serious pests of apple trees. This clone is sensitive to apple stem pitting virus and to apple stem grooving virus, but when used as a stock, it is compatible when grafted with virus-free scion cultivars such as 'Delicious' and 'McIntosh'. As a rootstock, this clone supports vigorous growth of the scion cultivar, making a "standard" tree; fruit production by the scion cultivar commences relatively early.

Asexual propagation of this new cultivar by grafting, as we have done in Ontario County, New York, has shown that these attributes are transmitted through succeeding asexual propagations.

The new variety is further as follows:

Tree: small, upright-spreading, vigor medium. Winterhardy under conditions at Geneva, New York. Very productive, with some tendency toward biennial bearing if not pruned.

Shoots: dark brown, stiff, usually short (ca. 30 cm). Pubescence is slight. Lenticels are medium in size, raised, tan, few. Axillary buds are sessile; may be either vegetative or mixed vegetative and fruit; most are appressed; bud scales are quite large on mixed buds. Completely free of burrknots and sphaeroblasts.

Leaves: lanceolate; margins coarsely serrate, but basipetal 1-4 leaves usually 1- to 3-lobed; apex acute, occasionally acuminate; base abrupt; lamella size averages 10 cm long×4 cm wide, but variable; lamella flat or slightly waved; stipules very small, usually 1-1.5 mm long. The tree is resistant to fire blight, crown rot, apple scab, pine vole and meadow vole. Sensitive to apple stem pitting and apple stem grooving virus. Susceptible to woolly apple aphids, European red mite and whiteflies.

The interstems, when employed, can be any compatible interstem interscion and include, for example, virus free selections of the clones Malling 9 (M.9) (also incorrectly called East Malling IX, Malling IX, EM IX, EM 9, M9, MIX, EM IX and EM.9); Budagovsky 9- ('Red-Leaved Paradise'), Budagovsky 57-491, Ottawa 3(0.3), Malling 26 (M.26), Malling 27 (M.27), Bemali, C6, Jork 9 (J9), P-1 (P-I), P-2 (P-II), P-16 (P-XVI), P-22 (P-XXII), 'Mark' (MAC-9), and Oregon Apple Rootstock No. 1, (OAR-1).

Where employed, an interstem clone is grafted onto the vole-resistant stock, usually approximately 30 cm above the soil level. A fruiting cultivar is grafted onto the interstem clone usually approximately 20 cm above the lower union. (It is noted the grafting is employed throughout herein, in its broadest sense and encompasses all the known techniques for forming an appropriate union between the two plant materials being joined.) The specific length of the interstem is not unduly critical to the scheme, but will affect the degree of tree size control obtained, as is understood by those skilled in the art. Preferably, the effective interstem, when grafted, is between 6 and 8 inches long (between graft unions). Usually, an interstem should have an effective length of at least about 4 inches to provide significant dwarfing. Effective interstem lengths above about 10 inches are usually not employed.

The fruiting cultivar employed can be any compatible apple bearing cultivar desired which is graftable to the vole-resistant rootstock and/or interscion. One can employ a "standard" fruiting cultivar or a "compact" fruiting cultivar. When one employs a standard" fruiting cultivar grafting of an interscion to control tree size is highly preferred. Where the fruiting cultivar is grafted directly to the vole-resistant rootstock, the use of a compact fruiting cultivar is preferred.

Standard fruiting cultivars include all fruiting cultivars with standard internode lengths, not "genetic dwarfs". Included are 'Delicious', 'McIntosh', 'Golden Delicious', 'Mutsu', 'Empire', 'Idared', 'Jonagold', 'Paulared', 'Northern Spy', 'Rome Beauty', 'Jerseymac', 'Jonamac', 'Cortland', 'Rhode Island Greening', and 'York Imperial', and all other standard-type sports of these and other cultivars.

Compact fruiting cultivars include sports of fruiting cultivars which differ from the parent strain in being inherently dwarfed, usually as shortened internode length and increased polar dominance. Included are: compact sports of 'Delicious': 'Red Chief', 'Miller Sturdee Spur', 'Starkrimson Delicious', 'Ace Red Delicious', 'Oregon Spur', and 'Red Spur'; compact sports of 'McIntosh': 'MacSpur', 'MorSpur', 'Dewar Spur' and 'StarkSpur'; compact sports of 'Golden Delicious': 'Starkspur Golden Delicious', 'YellowSpur', 'GoldSpur', 'MorSpur' and 'Tester Spur'; 'GranSpur' and other compact sports of 'Granny Smith'; 'Lawspur', and other compact sports of 'Rome Beauty'.

With reference to the Figures, five systems comprising the invention are hereinafter described in detail.

With reference to FIG. 1, one system of the invention comprises a vole-resistant Malus rootstock (on its own roots as subsequently employed), propagated asexually on its own roots by cuttage, by stooling, by nurse-root grafting or by micropropagation. An interstem clone is grafted into the vole-resistant stock, usually approximately 30 cm above soil level. A fruiting cultivar is grafted onto the interstem clone, usually approximately 20 cm above the lower union.

Figure 2:
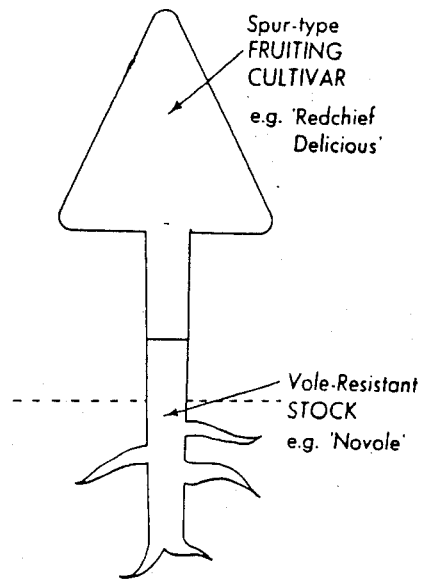

With reference to FIG. 2, a vole-resistant Malus clone, e.g. propagated asexually on its own roots. A fruiting cultivar, preferably a compact fruiting cultivar, is grafted onto the vole-resistant stock, usually about 30 cm above soil level.

Figure 3:
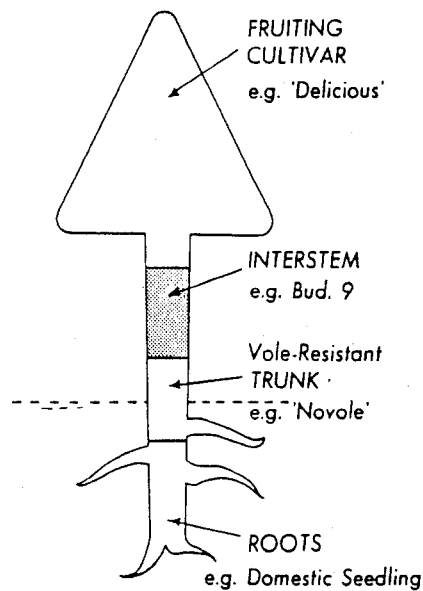

With reference to FIG. 3, a vole-resistant Malus clone is grafted onto a seedling or other rootstock. An interstem clone is grafted onto the vole-resistant clone usually about 50 cm above the lower union. A fruiting cultivar, preferably a standard cultivar, is grafted onto the interstem, usually about 50 cm above the lower union. A fruiting cultivar, preferably a standard cultivar, is grafted onto the interstem, usually approximately 20 cm above the interstem/vole-resistant clone union.

Figure 4:
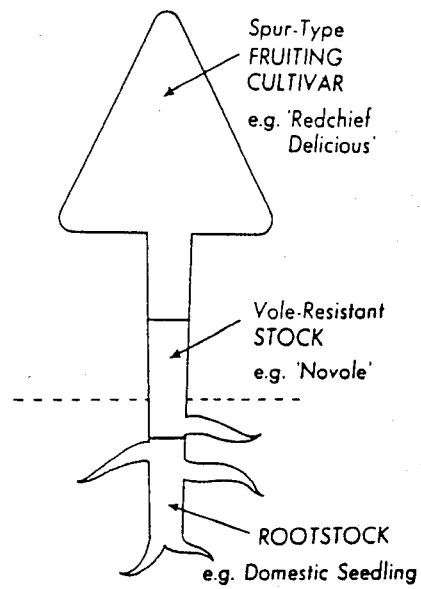

With reference to FIG. 4, a vole-resistant clone is grafted onto a seedling or other distinct desired rootstock. A fruiting cultivar, preferably a compact fruiting cultivar, is grafted on the vole-resistant clone usually approximately 30 cm above soil level.

The preferred trees of this invention, at substantially full height, preferably is between ten and fourteen feet tall.

In a fifth system not showing in the Figures, a vole-resistant clone can be bridge-grafted or inarched to repair damage done to an orchard apple tree by voles or other agents. The nature of the existing stock and scion is immaterial, except that the presence of apple stem pitting or apple stem grooving viruses could prevent satisfactory union. This latter proviso has applicability to all the systems above in that rootstock, interscion and fruiting cultivar should all be selected so that they are free of virus or other disease causing agents which would prevent or interfere with the production of an otherwise obtainable union and/or the survival of a healthy productive composite tree.

Techniques of propagation by grafting including seed germination, clonal rootstock, budding, whip grafting, top grafting, bridge grafting generally employable in this invention are known and are described, for example, by Way et al., "Propagating Fruit Trees in New York", Bulletin No. 817, May 1967, New York State Agricultural Experiment Station, Cornell University, Geneva, New York.

There follows an example of the invention. It should be understood that the invention is not limited to the details thereof.

EXAMPLE

Rooted cuttings of "Novole" (PI 286613) are planted in a nursery in early spring. In February, shoots 8 to 12 inches long are cut and treated with a rooting chemical, i.e. indolebutyric acid (IBA), packed in damp peat moss, and the bases warmed at about 70° F. for about three weeks. By about April 1, the rooted and rooting cuttings are planted in a nursery as liners (upper 2 or 3 inches exposed) in a standard nursery operation. Two or three buds develop into new shoots and in August, at a height of between about 12 to about 18 inches above soil level, a dwarfing interstem, Budagovsky 491, is bud-grafted to the rootstock. The grafting is done by traditional T-budding or by chip-budding. The following March, that portion of the rootstock which is distal to the graft is removed. The new interstem shoot is allowed to grow during the following summer and in August of this summer, the fruiting cultivar, e.g. 'Delicious' is grafted to the interstem about 8 inches above the union between the interstem and the rootstock. The following March, that portion of the interstem distal to the cultivator/interstem graft is removed. The following summer, the 'Delicious' bud grows and the following October or November, the composite tree is ready for digging and transplantation, for example, in a commercial orchard. A deposit with the intent of satisfying the requirement of the U.S. patent and Trademark Office Rules is located at the New York State Experimental Station, Cornell University, Geneva, New York; the role-resistant root stock which is the subject of co-pending application Ser. No. 391,897, filed June 6, 1983, being located in Orchard 24, row 1, trees 24 and 25, while a composite tree comprise said role-resistant stock as a root and trunk stock with a Budagovsky 491 interstem and a "Delicious" fruity cultivar is maintained in Nursury 107, row 10, section 18. These plant materials will be made available to the public in conformance with relevant Patent Statutes and Rules regarding living organisms.

We claim:

1. A composite apple tree comprising a fruiting cultivar grafted to an interstem cultivar which is in turn grafted to a 'Novole' rootstock.

2. A composite apple tree comprising a fruiting cultivar grafted to a 'Novole' rootstock.

3. The composite apple tree of claim 2 wherein the fruiting cultivar is a spur-type fruiting cultivar.

4. A composite apple tree comprising a fruiting cultivar grafted to an interstem cultivar, which is in turn grafted to a 'Novole' cultivar which is grafted to a rootstock which is obtained from a cultivar or a seedling.

5. A composite apple tree which comprises a fruiting cultivar grafted to a 'Novole' cultivar which in turn is grafted to a rootstock which is obtained from a cultivar or a seedling.

6. The composite apple tree of claim 5 wherein the fruiting cultivar is a spur-type fruiting cultivar.

7. A nursery stock material adapted to be grafted with a fruiting apple cultivar which comprises a Malus cultivar, adapted to serve as an interstem, grafted to a 'Novole' rootstock.

* * * * *